(12) United States Patent
Grziwa et al.

(10) Patent No.: US 11,129,971 B2
(45) Date of Patent: Sep. 28, 2021

(54) CHEST DRAINAGE SYSTEM

(71) Applicant: ATRIUM MEDICAL CORPORATION, Merrimack, NH (US)

(72) Inventors: Wolfram Grziwa, Mont Vernon, NH (US); Greg Peatfield, Atkinson, NH (US)

(73) Assignee: ATRIUM MEDICAL CORPORATION, Merrimack, NH (US)

(*) Notice: Subject to any disclaimer, the term of this patent is extended or adjusted under 35 U.S.C. 154(b) by 433 days.

(21) Appl. No.: 16/240,305

(22) Filed: Jan. 4, 2019

(65) Prior Publication Data

US 2019/0134363 A1 May 9, 2019

Related U.S. Application Data

(62) Division of application No. 15/151,116, filed on May 10, 2016, now Pat. No. 10,195,404.

(Continued)

(51) Int. Cl.
*A61M 1/00* (2006.01)
*A61M 27/00* (2006.01)

(52) U.S. Cl.
CPC .............. *A61M 27/00* (2013.01); *A61M 1/73* (2021.05); *A61M 2202/0225* (2013.01); *A61M 2205/3334* (2013.01); *A61M 2210/101* (2013.01)

(58) Field of Classification Search
CPC ............ A61M 1/73; A61M 2202/0225; A61M 2205/3334; A61M 2210/101; A61M 27/00
See application file for complete search history.

(56) References Cited

U.S. PATENT DOCUMENTS

| 4,654,029 A | 3/1987 | D'Antonio |
| 5,738,656 A | 4/1998 | Wagner |

(Continued)

FOREIGN PATENT DOCUMENTS

| CN | 86201261 U | 1/1987 |
| CN | 1720077 A | 1/2006 |

(Continued)

OTHER PUBLICATIONS

Australian Office Action dated Feb. 4, 2020 during the prosecution of corresponding Australian Patent Application No. 2016261628, 2 pages.

(Continued)

*Primary Examiner* — Kai H Weng
(74) *Attorney, Agent, or Firm* — Kevin T. Godlewski

(57) ABSTRACT

A chest drainage system, including a circulation assembly having an intake for taking fluid into the system and an exhaust for exhausting fluid out of the system. An intake flow device is configured to selectively control fluid flow through the intake and an exhaust flow device is configured to selectively controlling fluid flow through the exhaust. The circulation assembly has a first configuration and a second configuration such that transitioning between the first and second configurations during operation of the circulation assembly displaces at least a portion of fluid within the system with fluid from outside the system via the intake and the exhaust. A sensor is arranged in fluid communication with the fluid within the system and configured to detect a concentration of a reference fluid in the fluid in the system.

4 Claims, 7 Drawing Sheets

Related U.S. Application Data

(60) Provisional application No. 62/160,833, filed on May 13, 2015.

(56) References Cited

U.S. PATENT DOCUMENTS

| | | |
|---|---|---|
| 2003/0051733 A1 | 3/2003 | Kotmel et al. |
| 2004/0267215 A1 | 12/2004 | Charlez et al. |
| 2006/0025650 A1 | 2/2006 | Gavriely |
| 2006/0217685 A1 | 9/2006 | Shehada et al. |
| 2007/0250022 A1 | 10/2007 | Sirokman |
| 2008/0023005 A1 | 1/2008 | Tokunaga |
| 2009/0264833 A1 | 10/2009 | Boyle, Jr. |
| 2010/0130947 A1 | 5/2010 | Daly |
| 2011/0180064 A1 | 7/2011 | Tanaka et al. |
| 2013/0110057 A1 | 5/2013 | Croteau et al. |
| 2013/0165877 A1 | 6/2013 | Leeson et al. |
| 2014/0194835 A1 | 7/2014 | Ehlert |
| 2015/0031968 A1 | 1/2015 | Miserlis et al. |
| 2015/0174305 A1 | 6/2015 | Bharat |
| 2018/0104391 A1 | 4/2018 | Luxon et al. |

FOREIGN PATENT DOCUMENTS

| | | |
|---|---|---|
| CN | 101022847 A | 8/2007 |
| CN | 101111278 A | 1/2008 |
| CN | 201253371 Y | 6/2009 |
| CN | 103648537 A | 3/2014 |
| EP | 1572286 B1 | 5/2009 |
| JP | 2011523363 A | 8/2011 |
| WO | 2007024230 A1 | 3/2007 |
| WO | 2009120400 A2 | 10/2009 |
| WO | 2009135070 A1 | 11/2009 |
| WO | 2010134894 A1 | 11/2010 |
| WO | 2013123338 A1 | 8/2013 |
| WO | 2017155994 A1 | 9/2017 |

OTHER PUBLICATIONS

Chinese Office Action and Chinese Search Report (with English translations) dated Feb. 3, 2020 during the prosecution of corresponding Chinese Patent Application No. 201680036088.X, 16 pages.

Office Action issued in corresponding Japanese Application No. 2017-558532 dated Mar. 31, 2020, 11 pages.

Raffin, L., et al. "Assessment of end-tidal CO2 in the pleural chest tube during lung volume reduction surgery", Annales Francaises d'Anesthesi et de Reanimation (French Annals of Anesthesia and Intensive Care), May 2003, vol. 22, Issue No. 5, pp. 484-486 (English language abstract provided).

Oparka, Jonathan D., et al., "The application of capnography to differentiate peri-chest tube air leak from parenchymal leak following pulmonary surgery", Annals of Cardiothoracic Surgery, Mar. 1, 2014, vol. 3, No. 2, pp. 219-220.

International Search Report and Written Opinion dated Aug. 11, 2016 issued for corresponding International Application No. PCT/US2016/031623, 7 pages.

International Preliminary Report on Patentability dated Nov. 14, 2017 issued for corresponding International Application No. PCT/US2016/031623, 5 pages.

Extended European Search Report dated Feb. 18, 2019 issued for corresponding EP Application No. 16793364.7, 7 pages.

Office Action dated Mar. 7, 2019 issued for corresponding EP Application No. 16793364.7.

Notice of Allowance issued in U.S. Appl. No. 15/151,116, dated Sep. 25, 2018, 10 pages.

Office Action and Search Report issued in CN Application No. 201680036088.X dated Dec. 14, 2020, 15 pages.

Office Action issued in CN201680036088.X dated Jun. 15, 2021.

CHEST DRAINAGE SYSTEM

CROSS-REFERENCE TO RELATED APPLICATIONS

This application is a divisional of U.S. application Ser. No. 15/151,116, filed May 10, 2016, which claims the benefit of U.S. provisional application No. 62/160,833, filed May 13, 2015. Both U.S. application Ser. No. 15/151,116 and U.S. provisional application No. 62/160,833 are incorporated herein by reference in their entireties.

BACKGROUND

Chest drainage systems are known in the medical industry and used to treat patients by enabling drainage of a patient's pleural space following a traumatic event to the patient's lungs, such as surgery or injury. These chest drainage systems typically include a chest tube that is inserted into a patient's pleural space and a canister to collect fluids that drain from the pleural space. These fluids may include gases (e.g., air), liquids (e.g., blood, empyema, etc.), as well as any tissue or other solids associated therewith.

Currently, the decision as to when the chest drain system should be removed from a patient is subjectively determined on a case by case basis based on each particular medical practitioner's prior experience and patient outcomes. This may result in patients being left on a chest drain system too long, or removed too soon. Leaving a patient on too long will result in increased lengths of hospital stays, which may have a variety of undesirable effects such as associated increased medical costs for both the patient and medical care facility, less capacity for new patients, and decreased patient satisfaction due to long stays, while prematurely removing a patient may result in complications that require further medical attention and possibly readmission to the medical care facility.

SUMMARY

A chest drainage system, including circulation assembly having an intake for taking fluid into the system and an exhaust for exhausting fluid out of the system; an intake flow device configured to selectively control fluid flow through the intake and an exhaust flow device configured to selectively controlling fluid flow through the exhaust, the circulation assembly having a first configuration and a second configuration such that transitioning between the first and second configurations during operation of the circulation assembly displaces at least a portion of fluid within the system with fluid from outside the system via the intake and the exhaust; and a sensor arranged in fluid communication with the fluid within the system and configured to detect a concentration of a reference fluid in the fluid in the system.

A chest drainage system, comprising: a tubing circuit having a chest tube arranged to permit fluid to enter the tubing circuit; a circulation assembly having an intake flow device configured to selectively permit or impede fluid flow into the tubing circuit via an intake and an exhaust flow device configured to selectively permit or impede fluid flow out of the tubing circuit via an exhaust, wherein the circulation assembly is configured, via operation of the intake and exhaust flow devices, to transition between a first configuration that promotes fluid communication between the tubing circuit and an environment outside of the chest drainage system, and a second configuration that impedes fluid communication between the tubing circuit and the environment, such that a volume of the fluid within the tubing circuit is displaced out of the exhaust by fluid from the ambient environment entering the tubing circuit via the intake when the circulation assembly is in the first configuration; and a sensor in fluid communication with the tubing circuit and arranged to detect changes in a concentration of a reference gas in the fluid flowing through the tubing circuit as the circulation assembly transitions between the first and second configurations.

A method of using a chest drainage system including controlling fluid communication through an intake and an exhaust of a circulation assembly of the chest drainage system; displacing a volume of fluid within the chest drainage system by selectively permitting fluid from an ambient environment into the chest drainage system via the intake and exhausting fluid from the chest drainage system via the exhaust; and monitoring a concentration of a reference fluid in a fluid mixture within the chest drainage system with a sensor of the chest drainage system at a first time before the displacing and at a second time after the displacing.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures. The term "may" as used herein is intended to indicate optionality unless otherwise designated.

Figure 1:
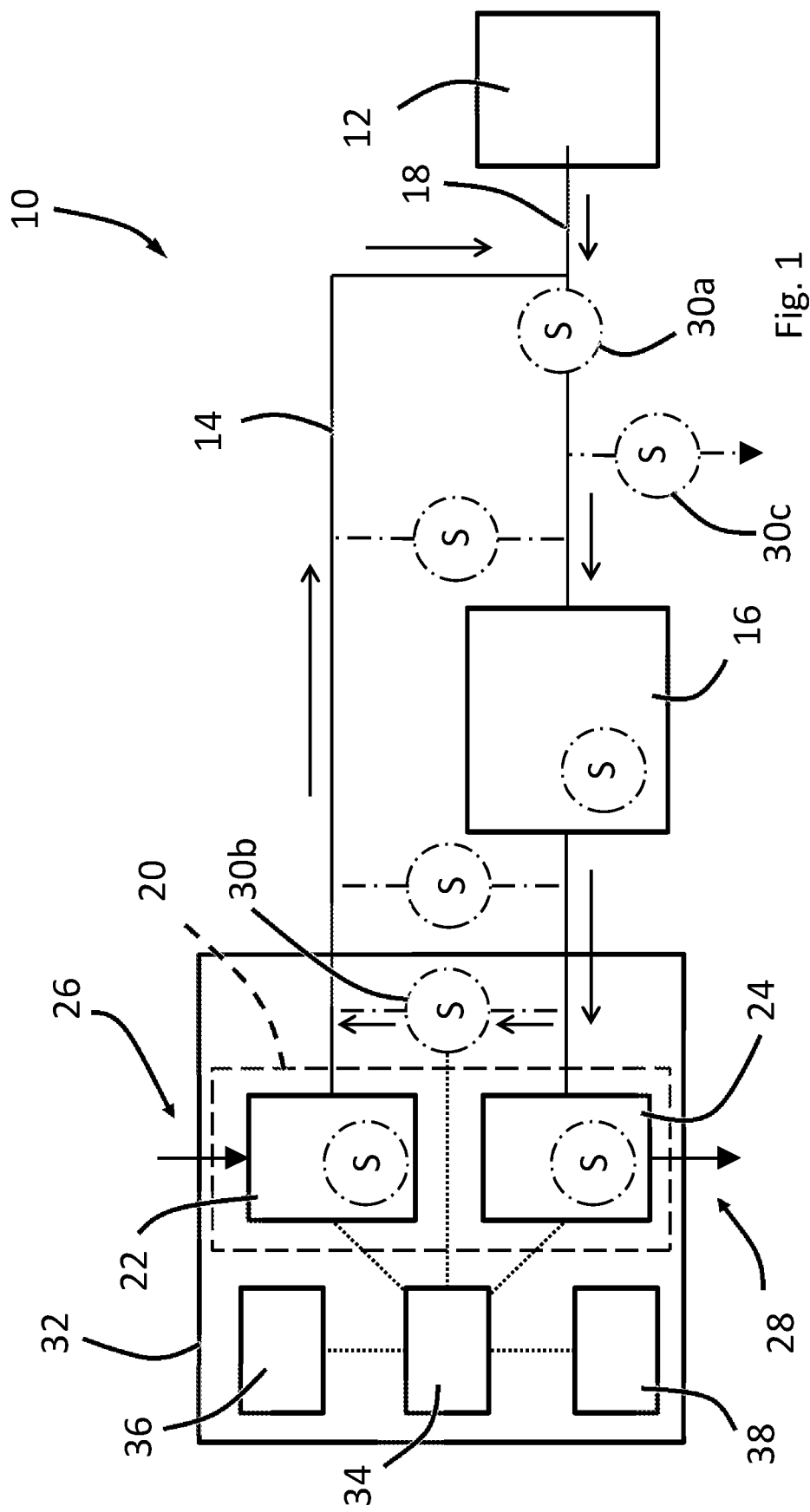
FIG. 1 schematically illustrates a chest drain system according to one embodiment disclosed herein.

Referring now to the drawings, a chest drainage system 10 is schematically illustrated in FIG. 1. The chest drainage system 10 is arranged to facilitate the drainage of fluid from the pleural space of a patient 12, following lung surgery or other traumatic event in which the lungs are punctured, cut, damaged or otherwise caused to leak fluid into the pleural space. The chest drainage system 10 may include any number or combination of components or features that are generally used by chest drainage systems known or devised in the art, some of which are discussed below. In addition to the below general description, various features and/or components that may be incorporated in whole or in part in any of the embodiments disclosed herein are discussed in U.S. Patent Publication No. 2013/0110057 to Croteau et al. ("the '057 Publication"), which is hereby incorporated by reference in its entirety.

The chest drainage system 10 according to the embodiment illustrated in FIG. 1 includes a tubing circuit 14 or tube set, having a canister 16 or other fluid collection vessel. It is noted that the term "circuit" as used herein does not necessitate that the circuit be formed as, or with, a complete cycle or loop, but instead, merely indicates that fluid flows through the circuit 14 in a set, desired, or predetermined manner, e.g., fluid is desirably carried away from the patient 12. It is also noted that the term fluid as used herein refers to a mixture of gases and/or liquids, but also generally includes to any solids or solid matter, e.g., clots of blood or tissue, which may flow or otherwise progress through the circuit 14 from the pleural space of the patient 12. A chest tube 18, which may alternatively be referred to as a thoracic catheter, drainage tube, etc., is located at the distal end of the tubing circuit 14, which is inserted into the patient 12. The chest tube 18 may be arranged according to any embodiment known or devised in the art, e.g., including a plurality of openings along its distal length to facilitate the flow of fluid into the tubing circuit 14 from the patient 12 without becoming clogged. The chest tube 18 may be an extension from a portion of the tubing circuit 14, attached to the tubing circuit 14 at or via a joint or juncture, etc.

The system 10 may include a circulation assembly 20 to selectively circulate fluid within the tubing circuit 14 and from the ambient environment into the tubing circuit 14. That is, to this end, the circulation assembly 20 includes a selective intake flow device 22 and a selective exhaust flow device 24, coupled to an intake 26 and an exhaust 28, respectively. The intake 26 and the exhaust 28 may be formed as or include any suitable port, hole, opening, or aperture that provides fluid communication between the tubing circuit 14 and the ambient environment, or atmosphere, outside of the tubing circuit 14. The terms ambient environment and atmosphere as used herein are interchangeable and intended to mean the volume of fluid, e.g. air, surrounding the chest drainage system 10 or otherwise located exterior to or outside of the tubing circuit 14. Typically, this is the ambient air in the room, e.g., hospital room, in which the chest drainage system 10 is being used. As discussed in more detail below, the fluid in the ambient environment or atmosphere may be utilized with the system 10 to shift the composition of fluid in the system 10 toward a known, estimated, or expected baseline composition. While ambient air is a readily available example of such a baseline fluid, it is to be understood that a user of the system 10 could pump, inject, or surround the system 10 with any desired fluid or fluid mixture, and correspondingly that any embodiment referencing ambient air could alternatively use any other baseline fluid that is provided from any desired source, e.g., a specific fluid vessel or container such as a syringe, the ambient air in the room in which the system 10 is located, etc.

The selective intake flow device 22 is arranged to selectively promote (e.g., passively or actively, as discussed below) and impede (e.g., block, stop, obstruct, hinder, or prevent) the fluid communication between the intake 26 and the tubing circuit 14, while the selective exhaust flow device 24 is arranged to selectively promote and impede the fluid communication between the exhaust 28 and the tubing circuit 14.

As noted above, "promote" may indicate active promotion of fluid flow, e.g., forcing, pumping, or urging fluid flow, or passive promotion, e.g., merely permitting fluid flow to occur. In one embodiment, at least one of the selective flow devices 22 and/or 24 passively promotes fluid flow therethrough. For example, in one embodiment, at least one of the selective flow devices 22 and/or 24 is, or includes, a valve that switches or transitions between an open position or configuration that passively promotes fluid flow by permitting fluid to naturally or freely flow therethrough and a closed position or configuration that impedes or blocks fluid flow. It is noted that the term "open" and "closed" are used relatively, and that in some embodiments the device 22 and/or 24 may be at least partially open when in the closed position, or at least partially closed when in the open position, but the degree of openness and closedness will differ between the two positions. Any type of valve known or discovered in the art may be included, e.g., check valves, electronically or sensor controlled valves, manually operated valves, etc. In one embodiment, a user may in effect create a valve by manually breaking open and then reclosing the tubing circuit 14 (e.g., disconnect two sections of tubing to open the circuit, then reconnect the two sections). In one embodiment, the selective flow device 22 and/or 24 may be or include components that are selectively connectable and disconnectable from the system 10, e.g., a syringe that is arranged to engage the tubing circuit 14 at the intake 26 and/or exhaust 28 in order to inject a baseline fluid into and/or remove trapped fluid from the system 10 before being disconnected from the system 10. Electronically or sensor controlled valves may be arranged to automatically open and/or close at set time intervals, upon on-demand instruction by a user (e.g., via the user pressing a corresponding electronic or physical button of the system), or upon measurement of one or more parameters or conditions sensed or measured within the chest drainage system 10 (e.g., pressure or pressure differential, gas concentration/composition, etc.).

In one embodiment, at least one of the selective flow devices 22 and/or 24 actively or forcibly promotes fluid flow therethough. For example, in one embodiment, at least one of the selective flow devices 22 and/or 24 is, or includes, a pump. While pumps and valves have different functions and arrangements, it is noted that in general, similarly to a valve, a pump will selectively promote flow therethrough when running (by forcibly moving fluid) and impede the flow of fluid therethrough when deactivated (e.g., the vanes, scrolls, plunger, gears, screw, piston, or other pumping mechanism of the pump will effectively block fluid flow when the pump is not running). In this way, both valves and pumps are considered selective flow devices, as are any other device, assembly, or mechanism that selectively promotes fluid flow in one configuration, state, or position, and impedes fluid flow when in another configuration, state, or position. For convenience in discussion, each of the selective flow devices 22 and 24 may be described herein as in an "open" position or configuration when promoting fluid flow (e.g., an open valve or running pump) and a "closed" position or configuration when impeding fluid flow (e.g., a closed valve or deactivated pump). During each operational cycle of the circulation assembly 20, the flow devices 22 and 24 may both act synchronously, or independently from each other. For example, in one embodiment both the flow devices 22 and 24 open and close at essentially the same time, which facilitates the maintenance of a static pressure within the system 10. In one embodiment, the intake flow device 22 opens first, raising the pressure within the system 10, and then, after the intake flow device 22 is closed, the exhaust flow device 24 is opened to exhaust fluid to reestablish a desired pressure within the system 10. In one embodiment, the device 24 is first opened, e.g., to drop pressure within the system 10, then the valve 22 thereafter opened to reestablish operational pressure within the system 10. Thus, it should be appreciated that the devices 22 and 24 may be opened and closed in any order (or reopened and reclosed multiple times) in order to achieve some desired result, such as to displace a desired volume of fluid, or maintain or achieve a desired pressure.

As discussed in more detail below, a sensor 30 may be included to detect the presence of one or more specified or selected fluids and/or the percentage or concentration thereof from a fluid mixture containing multiple fluid components. The sensors 30 may be arranged to also detect other parameters, such as pressure, pressure differential, temperature, air flow, etc., or additional sensors could be provided for this purpose. Various ones of the sensors 30 are identified with alphabetic identifiers (i.e., 'a', 'b', 'c') to facilitate discussion of specific embodiments, but it is to be understood that any reference to the "sensors 30" or the "sensor 30" is generally applicable to any and all of the sensors regardless of alphabetic identifier. The sensor 30 may be located at any location within the system 10 that is in fluid communication with the tubing circuit 14. A variety of optional or alternate locations for the sensor 30 are represented throughout the Figures with an encircled S drawn in phantom lines, which locations may be used for additional sensors 30, or as alternative locations for a single one of the sensors 30. In one embodiment, the readings from multiple sensors 30 are included at different locations throughout the system 10 and their readings compared, e.g., to determine whether the sensed fluid has equally distributed throughout the system 10. Thus, it is to be appreciated that any reference herein to embodiments referring to "the sensor 30" in the singular is intended to include any number of sensors.

In one embodiment, the sensor 30 is arranged with the tubing circuit 14 such that the sensor 30 passively senses fluid in the tubing circuit 14 as the fluid passes by the sensor 30. For example, the sensor 30a is shown "in-line" with the tubing circuit 14 which may promote passive sensing. Alternatively, the sensor 30 may be arranged (e.g., with a small fluid pump), to actively draw fluid to be sampled by the sensor 30. For example, the sensor 30b is illustrated bridging between locations of the tubing circuit proximate to the intake 26 and the exhaust 28 such that a portion of fluid can be actively drawn to the sensor 30b from the exhaust side and expelled to the intake side as indicated by arrows in FIG. 1. As another example, the sensor 30c is arranged to draw in fluid from the tubing circuit 14 and exhaust it to the ambient environment. Those of ordinary skill in the art will readily appreciate additional locations and/or configurations for the sensor 30.

The substance selected to be measured by the sensor 30 may be referred to herein as the reference gas, reference substance, or reference fluid. It is noted that various examples herein may specifically relate to a reference gas, but it is to be understood that this is for the sake of discussion only and that other fluids may be similarly monitored. It is noted that the fluid in the pleural space may have multiple phases, e.g., both gas and liquid. For simplicity in description and unless stated otherwise, the concentration of the reference substance, as the term is used herein, refers to the percentage of the reference substance in the relevant phase or phases being monitored by the sensor 30. For example, if the sensor 30 is arranged to only monitor gases and the fluid in the system 10 comprises both gases and liquids, then the concentration of the reference substance in the fluid refers to the percentage of the reference substance in the gaseous phase only, since the liquid phase is not monitored. In one embodiment, the reference substance is a gas and its concentration is determined via its partial pressure in the fluid mixture, although those of skill in the art will understand that any other method may be used.

In one embodiment disclosed herein, the sensor 30 can be used by a user to assist in determining when the patient 12 can safely be removed from the system 10 (e.g., when the leak in the patient's lung has healed sufficiently to permit removal of the patient 12 from the system 10). More specifically, it is understood by the current inventors that when a lung is healthy and undamaged (i.e., not leaking into the pleural space) the composition of the fluid in the lungs (e.g., the air exhaled by a person) will be isolated by patient tissue, e.g., the lung and pleural membrane, from the fluid in the pleural space. It is noted that some degree of diffusion or permeation of fluids through the pleural membrane may occur over time, but that the patient tissues regardless acts as a barrier to hinder or impede fluid transfer between the lungs and the pleural space, which barrier is not effective when the lung is damaged and leaking directly into the pleural space.

Figure 2:
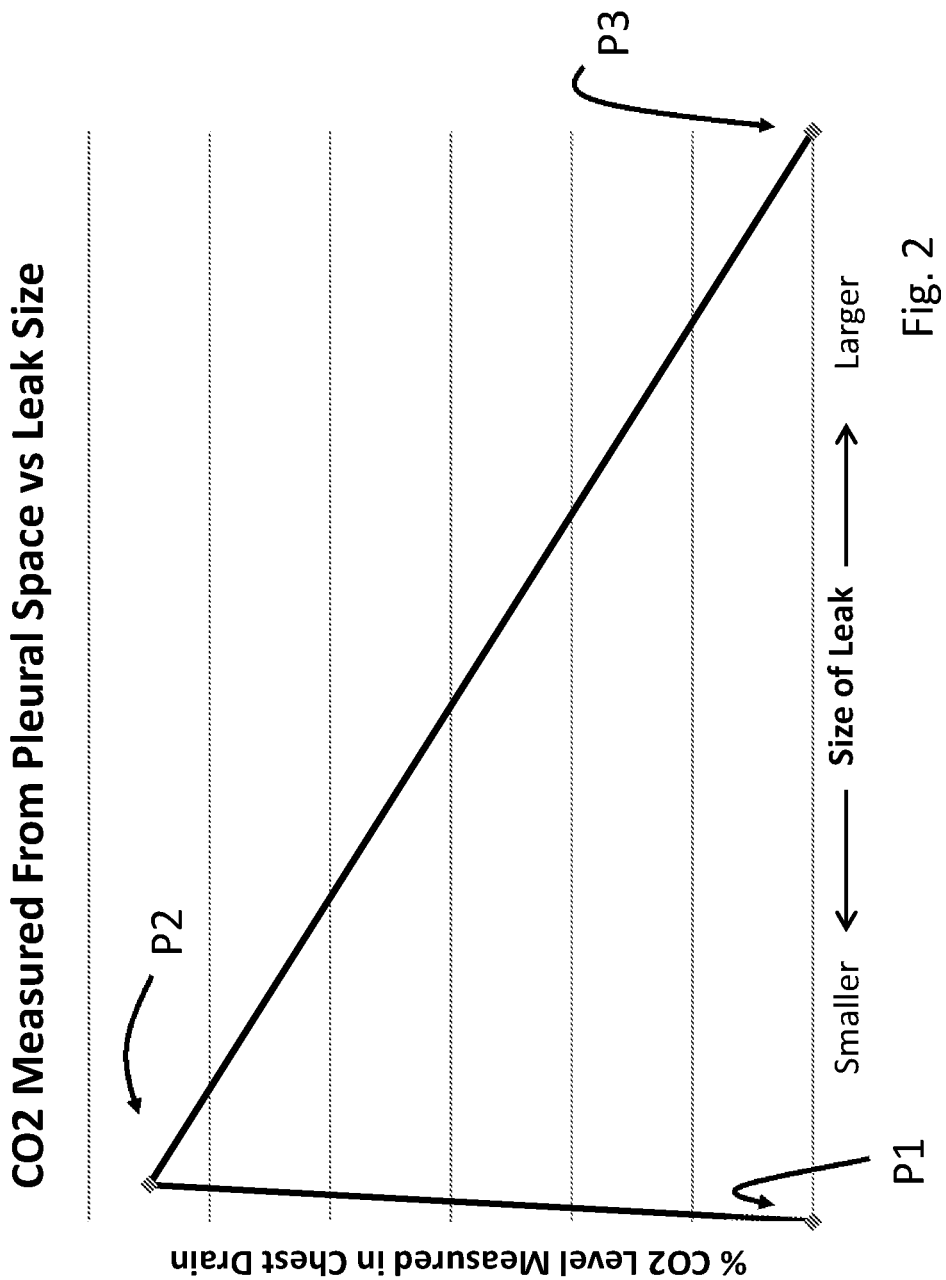
FIG. 2 illustrates an example graphical representation of carbon dioxide concentration expected to be found within the pleural space of a patient with respect to the size of a leak in the patient's lung.

As one example, absent a leak in a patient's lungs, the concentration of carbon dioxide ($CO_2$) of the air exhaled from a person's lungs, i.e., the end tidal $CO_2$, should be greater than the corresponding concentration of carbon dioxide in the gaseous phase of the fluid of that person's pleural space. However, if a leak exists, the concentration of $CO_2$ in the pleural space and the lungs would be expected to rise in correlation with the end tidal $CO_2$, as the fluid of the lungs leaks into the pleural space. However, it is noted that the size of the leak, and thus the rate of fluid leaked (volume or mass flow of leaked fluid per unit time), will also have an effect on the expected concentration of carbon dioxide found in the pleural space, as schematically illustrated in FIG. 2. It is to be understood that the graph of FIG. 2 should not be considered to scale, that the slope of the transitions between the points P1, P2, and P3 may be steeper, flatter, exponential, non-linear, etc., and thus this Figure is included for the sake of discussion only.

More specifically, as indicated by a point P1, when the leak is non-existent or negligibly small there will correspondingly be substantially no carbon dioxide leaking (or some base level amount corresponding to the natural permeation of carbon dioxide through a patient's tissues). When the leak is sufficiently large, as indicated by a point P3, the air inhaled by a patient simply passes through the leak in large quantities. Since the air is not held in the lungs, it does not have time to undergo the typical oxygen-carbon dioxide exchange within the lung and instead passes through having essentially the same composition as when inhaled (e.g., <1% $CO_2$). It is relatively easy for a trained medical professional to determine when a patient has a sufficiently large leak via traditional chest drainage systems and techniques (e.g., by monitoring the mass flow of gaseous fluid into the chest drain from the pleural space). However, when the leak is at some relatively small, yet still medically significant size (e.g., a "pin-hole leak"), as indicated by a point P2, it can be difficult for a medical professional to determine whether the leak exists since the flow of leaked fluid is relatively small. That is, in some instances, a leak may exist somewhere in the system (e.g., at a connection between tubing sections, through the incision through which the chest tube is inserted, etc.), but not in the patient's lungs, thereby making mass flow an unreliable indicator for lung leaks at low values. At and around this point P2, the inhaled air will only slowly leak from the lungs, thus providing oxygen in the inhaled air to have more time to undergo at least some degree of oxygen-carbon dioxide exchange within the lung, resulting in a relatively higher concentration of carbon dioxide leaking into the pleural space (e.g., between 4-6%, or otherwise approaching or approximating end tidal $CO_2$, which may be higher or lower than 4-6% depending upon the particular patient and/or the patient's use of a ventilator). Thus, in accordance with some of the embodiments disclosed herein, a determination of whether or not a leak is present may be assisted by monitoring the concentration of the $CO_2$ in the pleural space.

As another example of how the system 10 may be used to monitor the presence, non-presence, and/or healing status of a leak, the reference gas may be selected as a substance that is not expected to be commonly found within the body, e.g., helium or other non-toxic inhalable gas, anesthetic gases, etc., and the presence of that gas in the pleural space monitored to assist in determination of the presence of a leak, since this gas should only be found in the pleural space if leaked from the lungs. As another example, the reference gas may be selected as a substance that is expected to be commonly found within a patient, but at a higher than expected or unnatural concentration, e.g., the patient could inhale oxygen in concentrations greater than about 21% (naturally occurring percentage in air), and the pleural space monitored for changes in oxygen concentration and/or oxygen at higher than expected concentrations.

The circulation assembly 20 discussed above can be used in conjunction with the sensor 30 and other components of the system 10 to improve the accuracy and timeliness of leak and/or healing detection. That is, the inventors have determined that without the circulation assembly 20, and importantly without the intake flow device 22 to draw in new fluid, the pleural space fluid would be essentially trapped within the system (some small amount may be exchanged or removed, e.g., through pressure relief valves to maintain a set pressure within the system, or absorbed through tissues of the patient 12). A sensor arranged to sense the presence of a specific fluid, e.g., carbon dioxide, in a closed system will only indicate that a leak may have at some point in the past existed. Since the gas is trapped, such a system would not be useful for monitoring the condition of that leak over time or to assist in indicating when that leak has healed.

Advantageously, the system 10 includes the circulation assembly 20, which adds ambient air (or other baseline fluid, but referred to herein as ambient air for the sake of discussion) into the tubing circuit 14 via the intake flow device 22, and exhausts trapped fluid out from the tubing circuit 14 via the selective exhaust flow device 24, thereby effectively "resetting" the composition of the fluid in the tubing circuit 14. Since the ambient air has a known (or expected, but referred to herein as known for the sake of discussion) baseline composition, (e.g., ambient air is known or expected to have a composition of 21% oxygen, 78% nitrogen, 1% other), replacing at least some of the fluid within the tubing circuit 14 with ambient air (to reiterate, by exhausting some of the trapped fluid via the exhaust flow device 24 and adding ambient air via the intake flow device 22) will shift the composition of the fluid within the tubing circuit 14 to or toward the baseline composition of the ambient air.

For example, if a leak in the lung of the patient 12 exists, such that the fluid in the tubing circuit 14 comprises 5% carbon dioxide (example value only), replacing at least some of this trapped fluid with ambient air via the circulation assembly 20 will create a new mixture of fluid within the tubing circuit 14 that necessarily has less than 5% carbon dioxide, since ambient air typically comprises only a fraction of a percent of carbon dioxide. As time elapses between cycles of opening/closing the circulation assembly 20, the percentage of carbon dioxide or other reference gas in the fluid of the tubing circuit 14 will rise, due to partial pressures of the different components of the fluid, in proportion to the size of the leak (e.g., faster for larger leaks, slower for smaller leaks, or essentially no increase if the leak is healed). In this way, and as will be better appreciated in view of the below discussion, controlling operation of the circulation assembly 20 can be used to assist in monitoring and identifying changes in the composition of the fluid originating in the pleural space with the sensor 30, which may in turn be useful in more timely and accurately determining the presence, severity, and/or healing progress of a leak over time. Alternatively stated, use of the circulation assembly 20 may be used to improve the signal to noise ratio of the data measured by the sensor 30 by removing the "stale" or trapped reference fluid so it is easier to differentiate the "fresh" or newly leaked reference gas, which is most relevant for timely determining the status of the leak.

Referring back to the embodiment illustrated in FIG. 1, it can be seen that the sensor 30 may be located in signal communication with a control unit 32. As discussed in more detail below, the control unit 32 may house some or all of the electrical components for the system 10. In one embodiment, the control unit 32 is reusable (i.e., can be used for multiple patients), while the tubing circuit 14, canister 16, chest tube 18, etc., may instead be detachable therefrom and disposable. For example, filters or the like may be included, along with the canister 16, to catch fluids and prevent contamination of the control unit 32 to enable reusability. In this way, by including the sensor 30 as part of the control unit 32 (e.g., the sensor 30b), the sensor 30 is advantageously also reusable for subsequent patients.

In the illustrated embodiment, the control unit 32 includes a central processing unit (CPU) 34 or other logic unit to assist monitoring the concentration of the reference gas sensed by the sensor 30, performing computations or calculations on data measured by the sensor 30, controlling operation of the selective flow devices 22 and/or 24 (e.g., transitioning the flow devices between open and closed configurations) or other components of the system 10 during use thereof. The controller 32 may include a display unit 36 that displays various information to a user of the system 10, e.g., the condition of the selective flow devices 22 and/or 24, parameters measured by the sensor 30 and/or any other sensors (e.g., pressure of the fluid within the tubing circuit 14) included by the system 10, etc. A data storage medium device 38, e.g., memory, hard disk drive, solid state drive, etc., may be included to store the values measured by the sensor 30 over time, instructions or programs for controlling the operation of the system 10, etc. The control unit 32, CPU 34, and/or storage media device 38 may be used to sample the data measured by the sensor 30 at set time intervals, or in response to an event or events, such as before or after the opening and/or closing of the circulation assembly 20.

In one embodiment, the detected concentration of the reference gas is displayed by the display unit 36, e.g., numerically, graphically, tabularly, or representatively. Alternatively or additionally, the control unit 32 may use the data measured by the sensor 30 to perform further calculations, and the values resulting from such calculations displayed. In this way, the data measured by the sensor 30 may be directly (e.g., presented in raw form or without manipulation/calculations) or indirectly (e.g., after further calculations) used or displayed by the control unit 32. The data could additionally or alternatively be electronically retrieved from the system 10, e.g., "downloaded" in order to assist in clinical evaluation of that particular patient and/or to create historical trends to assist in the treatment of future patients. For example, the display unit 36 may be programmed with the CPU 34 to representatively display the data different colors, icons, symbols, characters, text, images, etc., that represent the concentration of the reference gas detected by the sensor 30. The CPU may alternatively and/or additionally be used to trigger an audible cue, sound, recorded message, etc., from one or more speakers coupled thereto. As one example, if the CPU 34 determines the presence or likely presence of a leak, e.g., based on the concentration of the reference gas measured by the sensor 30 as discussed further herein, a first color, e.g., blue, may be displayed by the display unit 36 to represent that the leak has been determined to exist, while a second color, e.g., green, may be displayed if it is determined that a leak does not exist. In one embodiment, a third color, e.g., white or gray, may be displayed if it is determined that a leak exists, but trends in the monitored data show that it is healing. In one embodiment, a real-time or regularly updated measured concentration of the reference gas is numerically displayed (e.g., the display 36 shows a numeral corresponding to the current percentage of the reference gas).

Figure 3:
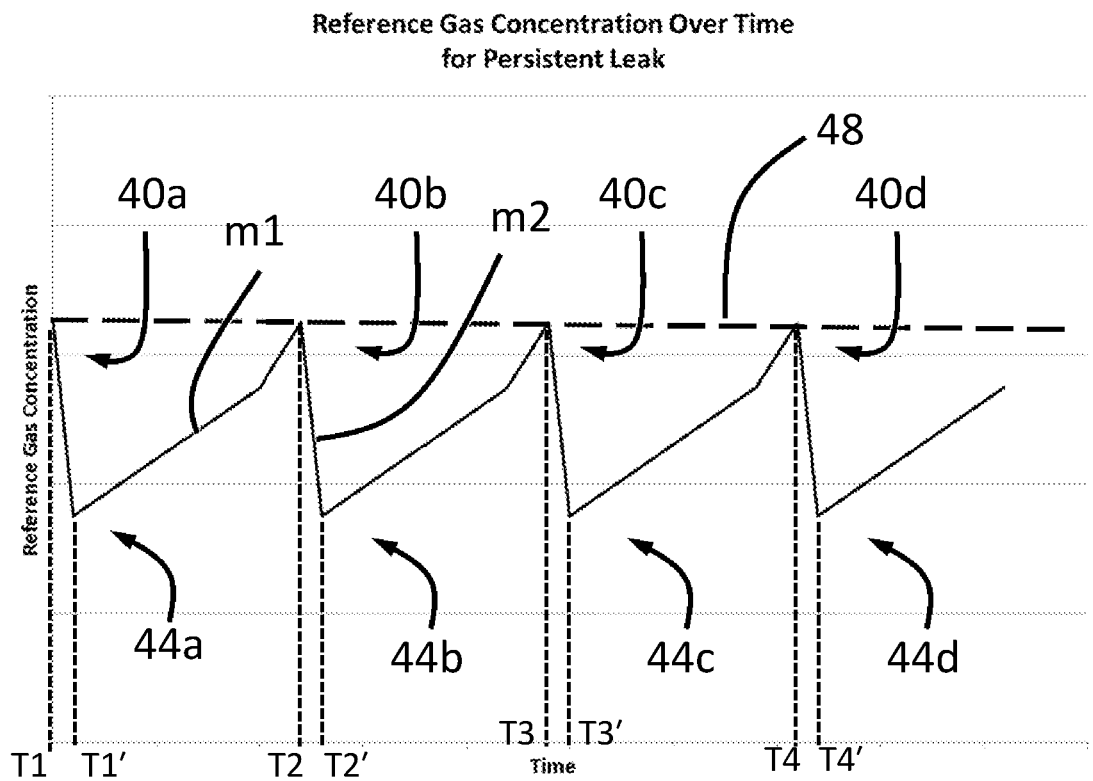
FIG. 3 illustrates an example graphical representation of data related to a patient with a persistent, non-healing leak.
Figure 4:
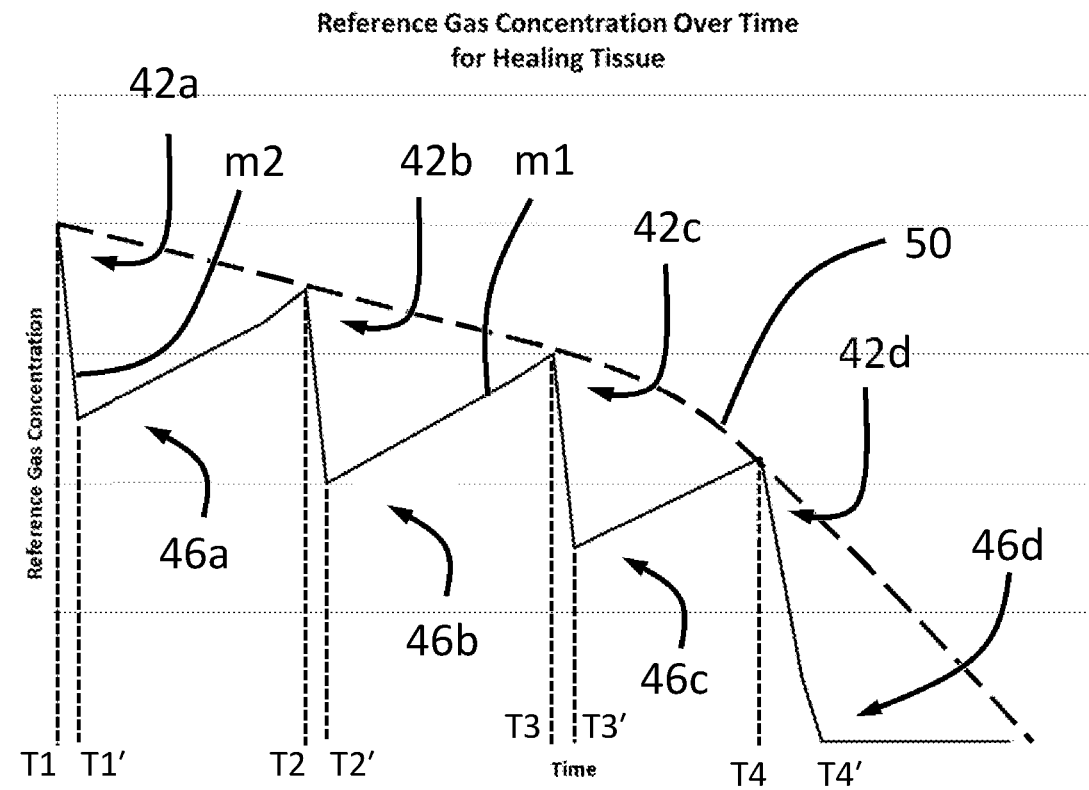
FIG. 4 illustrates an example graphical representation of data related to a patient with a healing leak.

In one embodiment, a graph showing the change in the measured concentration of the reference gas over a period of time is displayed by the display 36. The time period may be preprogrammed, selected (e.g., using a mouse to click on one of several preset options) or entered by the user (e.g., manually via a keyboard or touchscreen) into the control unit 32, or provided on demand in response to user input (e.g., the selective flow devices 24 and/or 26 will open and/or close each time a user presses a corresponding button). FIGS. 3 and 4 illustrate example graphs to assist in describing operation of the system 10 according to one embodiment. It is to be understood that the graphs of FIGS. 3 and 4 represent just one form that the information may be displayed by the display 36. FIGS. 3 and 4 are also useful to describe example scenarios in which the system 10 may be used to determine if a leak exists, the severity of the leak, and/or whether and how quickly the leak is healing over time. It is noted that in FIGS. 3 and 4 the baseline amount corresponding to a fully healed condition is when the reference gas concentration drops to zero, such as for certain reference gases such as helium. However, it is to be understood that in other embodiments the baseline fluid may be selected such that the reference fluid concentration is a non-zero value when the patient is fully healed (such as occurs when the reference gas is oxygen), or that the reference gas concentration may increase over time as the leak heals, depending on the baseline fluid and reference fluid that are selected.

In FIGS. 3 and 4, the opening of the circulation assembly 20 corresponds to a set of times T1-T4, while the closing of the circulation assembly 20 corresponds to a set of times T1'-T4'. If the lung of the patient 12 has a leak, the concentration of the reference gas will rise over time when the circulation assembly 20 is in its closed configuration (i.e., between each closing time and the corresponding subsequent opening time, e.g., T1'-T3' corresponding with T2-T4 respectively; each such interval may be referred to herein as a closed cycle for the circulation assembly 20). This behavior is expected because the reference gas will leak from the lungs into the pleural space, and from the pleural space distribute evenly throughout the rest of the tubing circuit 14 in accordance with its partial pressure.

Oppositely, the concentration of the reference gas in this embodiment drops when the circulation assembly 20 is in its open configuration (i.e., between each opening time, e.g., T1-T4 and the subsequent closing time e.g., T1'-T4') since opening of the circulation assembly 20 enables trapped fluid within the tubing circuit 14 to be replaced by ambient air as described herein. Accordingly, the concentration of the reference gas for each operational cycle of the circulation assembly 20 reaches a local maximum 40a-40d (collectively, the maxima 40) in FIGS. 3 and 42a-42d (collectively, the maxima 42) in FIG. 4 at the times T1-T4, respectively, just before the circulation assembly 20 is opened (i.e., before ambient air replaces at least some of the trapped fluid). Similarly, the concentration of the reference gas reaches a local minimum 44a-44d (collectively, the minima 44) in FIGS. 3 and 46a-46d (collectively, the minima 46) in FIG. 4 at the times T1'-T4', respectively, just after the circulation assembly 20 is closed (i.e., after the fluid is again trapped and any reference gas communicated to the system 10 through a leak in the lungs of the patient 12 begins to build up).

The length of time between cycles may be determined on a case-by-case basis based on the specific geometry of the system 10 and/or volume of the tubing circuit 14, desires of the user, etc. For example, larger volumes, more complicated geometry, longer lengths of tubing, or the distance of the sensor 30 from the patient 12, may result in the reference gas taking longer to reach the sensor 30 in a meaningful amount. Thus, the cycles in one embodiment may be set to occur infrequently enough that the reference gas has sufficient time to reach the sensor 30 in measurable quantities if an insufficiently healed leak exists. In one embodiment, the circulation assembly 20 aids in delivering the reference fluid or gas to the sensor 30 as the fluid within the tubing circuit is urged from the intake 26 to the exhaust 28. If a predetermined amount of reference gas builds up or fails to build up, as measured at the sensor 30 during or between each cycle of operation of the circulation assembly 20, it can be determined that the leak has completely or at least sufficiently healed.

It is noted that the sensor 30a is particularly advantageous in some embodiments as it is very close to the patient 12, while still being directly in fluid communication with the fluid circulated by the circulation assembly 20 within the fluid circuit 14. That is, having the sensor 30a located close to the patient 12 will reduce the amount of time needed for the reference gas to reach the sensor 30a, thereby increasing the timeliness in the accuracy of its readings. It is noted that the sensor may be positioned in some embodiments within the chest tube 18, and thus be even closer to the leak, but then the sensor would only be indirectly in communication with the fluid circulated by the circulation assembly 20 (and thus, there may be a higher likelihood of trapped fluid within the pleural space as opposed to the tubing circuit 14, which pleural space cannot directly be systematically reset back to or toward a baseline via the circulation assembly 20 as discussed herein). The sensor 30a may communicate wirelessly with the control unit 32, via wires extending interiorly or exteriorly along the length of the sections of the tubing circuit 14, via an external reading device in communication with the control unit 32, etc.

Referring back to FIGS. 3 and 4, it can be appreciated that FIG. 3 illustrates an example scenario in which a leak is persistent and not healing, while FIG. 4 illustrates an example scenario in which a leak is healing over time. That is, it can be seen from a preliminary review of FIG. 3 that the concentration of the reference gas keeps rising, while the concentration of the reference gas in FIG. 4 steadily drops until it remains at zero after time T4' (a zero concentration in this example corresponding to a healed leak, since without the leak the reference gas will not be present in the tubing circuit 14). Since a leak is present in both scenarios, it can be seen that the concentration of the reference gas increases between each operational cycle of the circulation assembly 20. However, as can be seen by comparing FIGS. 3 and 4, the concentration of the reference gas returns to a generally consistent value after each cycle when the leak is not healing (e.g., the maxima 40a≈40b≈40c≈40d), while the concentration of the reference gas decreases relatively for each cycle when the leak is healing (e.g., the maxima 42a>42b>42c>42d). That is, the volume of reference gas that leaks through a non-healing leak should be consistent over a given length of time, since the volume of gas leaked is a function of the size of the leak. In this way, if the time between each cycle is kept consistent, it is expected that concentration of the reference gas between each operational cycle of the circulation assembly 20 will return to approximately the same value (i.e., within some relatively small or acceptable percent), as illustrated in FIG. 3. Oppositely, a healing leak will decrease in size as it heals, which should accordingly result in a lesser volume of leaked reference gas through the leak over a given time period as it heals. A leak that is actively healing should result in a decreasing concentration of reference gas over time as the circulation assembly 20 continues to cycle, as illustrated in FIG. 4.

It is noted that since healing may be relatively slow (e.g., on the order of days) and that the cycles may be relatively fast (e.g., on the order of minutes), it may take numerous cycles of the circulation assembly 20 before a measurably significant decrease in the reference gas concentration is noted. For example, in one embodiment the circulation assembly is cycled about every five to thirty minutes, and in a further embodiment, about every ten minutes, although other times may be used in other embodiments. Thus, FIG. 4 represents an exaggeratedly fast case useful for the ease of discussion only and does not likely represent a realistic healing profile, which may include hundreds or thousands of cycles.

Additional analysis may be performed, e.g., by the control unit 32 to help control operation of the system 10 and/or determine healing status of the patient 12. To this end, the control unit 32 may consider natural phenomenon, constants, and/or physical laws, such as the ideal gas law, i.e., PV=nRT, where P is pressure, V is volume, n is the amount (moles) of gas, R is the ideal gas constant, and T is temperature. The control unit 32 may also consider equations specifically related to the system 10, e.g., such as that the total volume equals the sum of the volumes of the patient 12, the tubing circuit 14, the canister 16 (or empty portion thereof), and the chest tube 18. That is, $V_{total} = V_{patient} + V_{circuit} + V_{canister} + V_{chest\ tube}$. Under normal circumstances, (e.g., the patient 12 resting in bed), $V_{patient}$, $V_{circuit}$, and $V_{chest\ tube}$ should remain constant. Initially (e.g., following trauma to the patient's lungs and insertion of the chest tube 18), a substantial amount of liquids may be produced by the patient and fill the canister 16. During this time period, the volume $V_{canister}$ may change as it fills with solids and liquids from the patient 12. However, any such change is readily measurable, e.g., via a level sensor disposed with the canister 16. Additionally after this initial time period, patients largely cease producing liquids, and thus the empty volume $V_{canister}$ of the canister 16 is also constant. In either case, $V_{total}$ may be considered a "known" parameter as it component volumes are either constant, or measurable.

In one embodiment, the control unit 32 can calculate an expected concentration of the reference gas ($C_{expected}$) after any given cycle "n" of the circulation assembly for comparison with actually measured concentration data ($C_{measured}$). It is to be appreciated that this calculated value $C_{expected}$ may be used as the aforementioned baseline composition with which conformity is desired in order for the system 10 to indicate a healed status, and/or used in conjunction with some other baseline. In one embodiment, the control unit 32 may utilize the following equation:

$$C_{expected} = C_{measured} * \left[1 - \frac{V_{displaced}}{V_{Total}}\right]$$

where $C_{measured}$ is the current gas concentration measured by the sensor 30 for any given cycle "n" prior to opening the assembly 20, $V_{displaced}$ is the volume of fluid displaced during the open cycle of the assembly 20, and $V_{total}$ is defined as discussed above. For example, $V_{displaced}$ may be determined by monitoring the volume of fluid entering the system 10 via the intake 26 and/or exiting via the exhaust 28, e.g., via one or more mass or volumetric flow sensors. In one embodiment, $V_{displaced}$ is actively controlling the circulation assembly 20 to permit only a set amount of fluid into the system 10 via the intake 26 (e.g., closing or shutting off the intake flow device 22 after the set amount of fluid has been detected as entering through the intake 26). In one embodiment, discussed in more detail below with respect to FIG. 6 and in general accordance with embodiments disclosed in the '057 Publication incorporated by reference herein above, a vacuum accumulator may be included to pull a specific amount of fluid into the system 10, as determined by the capacity of the accumulator.

In accordance with the ideal gas law, pressure and/or temperature sensors may be included to account for any variance in these parameters. Assuming consistency with the ideal gas law, one would expect (after the reference gas has had sufficient time to redistribute and reach equilibrium throughout $V_{total}$ in accordance with its partial pressure) the value of $C_{expected}$ calculated for any given cycle, i.e., cycle "n", of the circulation assembly 20 to equal the value of $C_{measured}$ for next cycle, i.e., cycle "n+1". That is, the above equation relies on the system being volumetrically closed during the closed cycle time of the circulation assembly 20 (i.e., when the intake flow device 22 is closed, it is assumed that no fluid is entering the system 10). However, if a leak exists, then $V_{total}$ would as well include the volume of fluid leaked into the pleural space ($V_{leak}$), which is not taken into account by the above equation. Therefore, deviation from this equation is indicative of a leak. Furthermore, the magnitude of the difference between the calculated expected concentration $C_{expected}$ and the actual measured concentration $C_{measured}$ (ΔC), is further indicative of the size of the leak (e.g., larger leaks leading to potentially greater deviation). Thus, by monitoring the change in this difference ΔC over time (i.e., taking the first derivative d(ΔC)/dt), the control unit 32 may further track the healing status of the leak over time. That is, the closer ΔC is to zero, then the closer $C_{expected}$ for cycle "n" is to $C_{measured}$ for cycle "n+1", and in turn the closer the above equation is to correctly describing the actual scenario. Since the equation assumes no leak, increased conformance with the equation thereby indicates healing.

In one embodiment, the circulation assembly 20 is arranged to intake and exhaust a volume of air at least as large as the volume within the tubing circuit 14 and the canister 16 (e.g., $V_{displaced} \geq V_{tubing} + V_{canister}$), such that the baseline is significantly reestablished within the tubing circuit 30. However, the intake and exhaust of any other volume will nevertheless result in a measurable relative change in the composition of the fluid within the tubing circuit 14 back toward the known baseline. If the concentration of the reference continues after numerous cycles of the circulation assembly 20 to deviate from the baseline (and/or from a threshold value corresponding to the baseline or other parameter as discussed in more detail below), or does not decrease sufficiently over a suitably significant period of time or number of cycles, it can be determined that the leak persists. If substantially no deviation from the baseline (and/or threshold value) occurs over a suitable length of time or number of cycles (e.g., if desired by a user, some relatively minor deviation that lies within a tolerance amount may be permitted), then it can be determined that the leak has healed.

The results monitored by the sensor 30 may be compared, e.g., either manually by a user of the system 10 (e.g., if communicated to the user via the display 36) or utilizing the CPU 34, directly or indirectly (e.g., performing a calculation on the measured data in an intermediate step and comparing the result of that calculation) to a threshold value to evaluate the presence, severity, and/or healing status of a leak in the lungs of the patient 12. If the CPU 34 is used to perform this comparison, the threshold value may be stored by the data storage medium device 38. In one embodiment the threshold value may correspond to the concentration of the reference gas in the baseline composition of ambient air. For example, the threshold value may be set at about 21% if the reference gas is oxygen, about 0.00% if the reference gas is helium, about 0.04% if the reference gas is carbon dioxide, etc., which correspond to the relative percentages of these gases typically found in ambient air. Instead of setting the threshold value as the absolute value of the reference gas concentration, it could be set as an offset or difference. For example, the data measured by the sensor 30 immediately following the opening of the circulation assembly 20 (e.g., when the ambient air is directed to the sensor 30) may be compared to the data measured immediately preceding the next opening of the circulation assembly (e.g., after the reference gas, if there is still a leak, has had time to build back up in the system). As another example, an additional sensor resembling the sensor 30 may be included exterior to the tubing circuit 14, or proximate to the intake 24 (and thus, measure the baseline), and its measured data compared to the data measured by the sensor 30 to calculate a difference therebetween, which difference is then compared to the threshold value. In accordance with the above-discussed equation for $C_{expected}$, the threshold value may be set for $\Delta C$ and a healed status determined if $\Delta C$ is less than and/or equal to the threshold value. In one embodiment, there may be multiple threshold values that need to be met for a variety of different parameters in order for the system 10, e.g., via the control unit 32, to determine a fully healed status.

In one embodiment, the threshold value can be set as the amount of the reference gas expected to be found in the tubing circuit 14 if the leak is of an impermissibly large (unhealed) size. For example, the threshold value in this example may be calculated based on the historical data or trends, particular physiological parameters of the patient, such as lung capacity, end tidal $CO_2$, etc., or any other relevant parameters. In one embodiment, the threshold value may be preset and stored in the storage media device 38. In one embodiment, the threshold value may be entered or input by a user of the system 10, e.g., via a selector dial, mouse, keyboard, press button, touchscreen, etc. or other input device coupled to the control unit 32. In one embodiment, the threshold value may be determined "on-the-fly" based on the past data gathered by the sensor 30. For example, the threshold value may be set as a previous maximum, minimum, or some other measured or calculated value of the reference gas concentration (e.g., one of the maxima 40 of FIG. 3 and/or the maxima 42 of FIG. 4), which is compared to the most recent maximum measured by the sensor 30 (e.g., at the time T4 compare the maximum 40*d* to any of the previous maxima 40*a*-40*c*, or the maximum 42*d* to any of the previous maxima 42*a*-42*c*). Advantageously, the system 10 does not have to be carefully calibrated if it does not rely on preset or user entered values (since only the relative nature between the measured data is considered). Regardless of the manner by which the threshold value is set, it can be determined that a leak is still present by performing comparisons of the data measured by the sensor 30 to the corresponding threshold values.

The creation of a trend line may also be useful in determining the presence and/or healing status of a leak, i.e., either in lieu of or in addition to the use of a threshold value. The trend line may be displayed by the display 36, calculated by the CPU 34, stored by the storage media device 38, etc., or any combination thereof. For example, referring back to FIGS. 3 and 4, a trend line 48 is shown in FIG. 3 and a trend line 50 is shown in FIG. 4. The trend lines 48 and 50 in these embodiments are drawn connecting the local maxima 40 and 42, respectively, for FIGS. 3 and 4. Alternatively, the local minima 44 and/or 46 may be used, or some average or weighted value between the maxima and minima. As illustrated in FIG. 3, the trend line corresponding to a non-healing leak, e.g., the trend line 48, will be essentially flat, or have a slope of zero, while the trend line corresponding to a healing leak, e.g., the trend line 50, will have a negative slope. Thus, it is to be appreciated that the CPU 34 may be used to calculate and/or compare the slope of a trend line to assist in determining whether a leak is healing.

Trend lines as discussed above may additionally be helpful in determining the rate of healing of a leak and/or the estimate or forecast as to when a leak is likely to be healed. For example, if the slope of a trend line is negative, thereby indicating healing, it may be extrapolated or estimated according to any known or developed extrapolation or estimation methods to determine when the reference gas concentration is likely to fall below a threshold value. Parameters useful in such a calculation may include the magnitude of the most recent measured maximum of the reference gas concentration or average of a given number of previous maxima, the magnitude of the most recent measured minimum of the reference gas concentration or average of a given number of previous minima, the slope of the trend line, the change in the slope of the trend line over time or difference between instantaneous slopes of the trend line at different points over time, etc. These predictions may additionally be compared against actual results to determine their accuracy as well as to generate historical healing data that may be considered in future calculations.

In view of the above, those of ordinary skill in the art will appreciate that processing of the measured reference gas concentration or partial pressure data can be done to reduce the raw measured data into more clinically relevant data. As noted above, some examples include displaying the minimum, average, and/or maximum of the reference gas concentration over a sample period (related to time, number of cycles, or other event) and associated statistical values such as standard deviation, sample variance, etc. Trends or moving averages can be forecast or extrapolated to predict when a patient might be healed well enough to be sent home and/or disconnected from the system 10. These values may be displayed directly for clinical review, e.g., via the display 36, or not displayed but utilized by the CPU 34 to calculate one or more values that are displayed, such as Rate of Change, Estimated Time to Closure (patient healed), a visual or subjective scale of patient leak (for example, they may be categorized as major, minor, small, none). Those of ordinary skill in the art will recognize other visual and/or auditory indicators that can be used to designate that a patient has healed, is healing, the rate of healing, etc.

The rate of change/delta change of the reference gas concentration during each open or closed cycle of the circulation assembly 20 (i.e., the slope of the measured data between a minimum and the subsequent maximum, as indicated in FIGS. 3-4 as a slope m1, and/or the slope of the measured data between a maximum and the subsequent minimum, as indicated in FIGS. 3-4 by a slope m2) corresponds to how quickly or slowly the reference gas is being removed and/or building back up, and thus may also be used to indicate the difference between the composition of fluid in the patient 12 and the composition of fluid in the chest drainage system 10. In addition to the slopes m1 and m2 of FIGS. 3-4, which are shown in a simplified form merely connecting each minimum to the subsequent maximum, it is noted that the actual buildup of the reference gas over time may occur non-linearly, and the instantaneous slopes taken at given points of time, e.g., directly following and/or preceding the transition of the circulation assembly 20 between the open and closed configurations, may also provide useful information as to the healing status of a leak. For example, it is noted that the buildup of reference gas may in some embodiments likely follow an asymptotic growth function, e.g., an increasing form of exponential decay, which may have the general equation $C=A(1-e^{-kt})$, where C is the concentration, A is the asymptotic upper bound, e is Euler's number, k is a growth constant, and t is time.

Figure 5:
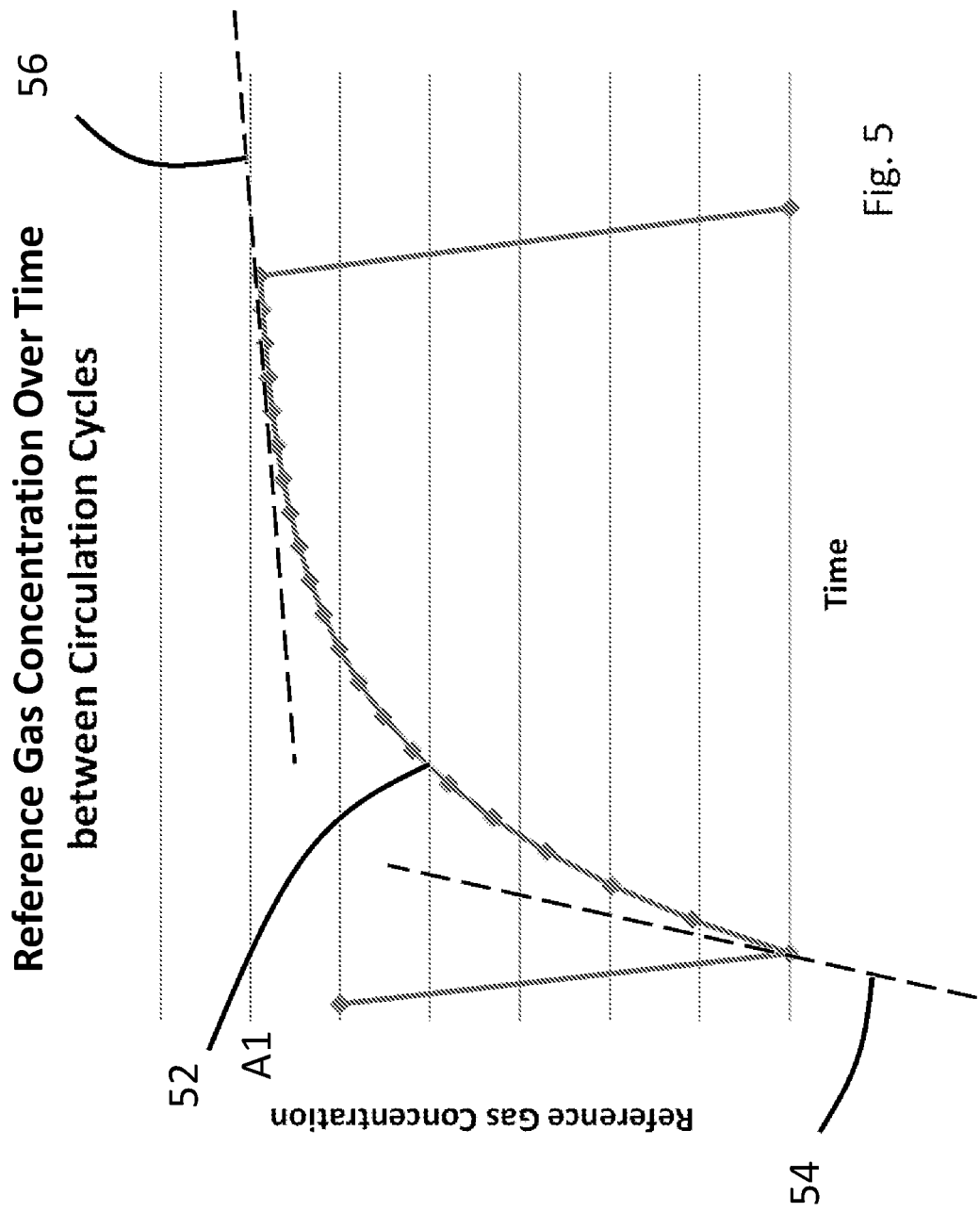
FIG. 5 illustrates an example graphical representation of reference gas concentration data over time between operating cycles of a circulation assembly.

FIG. 5 illustrates an example curve 52 corresponding to the buildup of reference gas over time between circulation cycles of the circulation assembly 20 (that is, when the circulation assembly 20 is in its closed configuration after transitioning from the open configuration and before transitioning back into the open configuration), thereby corresponding generally to the portion of data represented by the simplified slope m1 of FIGS. 3-4. In other words, the curve 52 may be a more realistic representation of the raw data of the reference gas concentration over time, which is more simply represented by the slope m1.

The curve 52 is illustrated asymptotically approaching a value A1 and having an initial instantaneous slope 54 (i.e., at or near the local minimum, corresponding to the behavior directly following the transition of the circulation assembly 20 from the open configuration to the closed configuration) and a final instantaneous slope 56 (i.e., at or near the local maximum, corresponding to the behavior directly preceding the transition of the circulation assembly 20 from the closed configuration back to the open configuration). Any or all of these values may be useful in determining whether a leak has healed and/or for monitoring the healing status of the leak over time. For example, the asymptotic upper bound values, e.g., A1, may be useful for comparison to a known or expected baseline composition as discussed above, with continued deviation away from the baseline value after multiple cycles of the circulation assembly 20 indicating the persistence of a leak as discussed herein.

The initial instantaneous slope, e.g., 54, is indicative of the rate of change in the reference gas concentration directly after the circulation assembly 20 is closed. Since the fluid in pleural space of the patient 12 is not directly located in the path between the intake 26 and the exhaust 28 (only connected via the chest tube 18), the fluid in the pleural space may hold a higher than average concentration of the reference gas following a cycle of the circulation assembly 20 until the reference gas has sufficient time to redistribute throughout the system 10 in accordance with its partial pressure. Thus, the initial instantaneous slope 54 would be expected to be steeper if a relatively large amount and/or relatively higher concentration of reference gas is located in the pleural space, since the correspondingly higher partial pressure would cause a more rapid distribution thereof.

The slope 56 is indicative of the rate of change in the reference gas concentration immediately before the circulation assembly 20 is again opened. If following an asymptotic function, the slope 56 would thus be expected to have a value very close to zero when the reference gas has reached equilibrium throughout the system 10. This can be particularly useful in embodiments in which the sensor 30 is located distantly from the patient 12 (which, as discussed above, would increase the time needed for the reference gas to reach the sensor 30) and/or for determining, e.g., automatically via the control unit 32, how often the circulation assembly 20 should be cycled. For example, in one embodiment, the circulation assembly 20 is not re-opened until the slope 54 has decreased below some corresponding threshold amount (or alternatively stated, the decreasing of the slope 56 below a threshold amount triggers cycling of the circulation assembly 20), thereby providing confidence that the sensor 30 has accurately recorded the actual concentration of the reference gas at system equilibrium. In one embodiment, the circulation assembly 20 utilizes the slope 56 to trigger or permit opening of the circulation assembly 20 every so often, e.g., every "x" number of cycles, but for all other cycles operates in some other manner, thereby utilizing the slope 56 to occasionally recalibrate the system 10 and/or establish a degree of confidence in the data measured during the other cycles. In one embodiment, the circulation assembly operates at a plurality of different time intervals (e.g., randomly generated, preset, etc.) and the slope 56 from each cycle is compared to each other to determine whether certain cycles are occurring too fast (e.g., the reference gas is not fully equalizing for certain time intervals as indicated by a relatively steeper slope) or too slow (e.g., the time between cycles could be decreased to increase sensing fidelity in the system 10). In this way, it should be appreciated that the control unit 32 may be used to automatically adjust the operation and/or cycle time for the circulation assembly 20 based at least in part on the slope 56.

Figure 6:
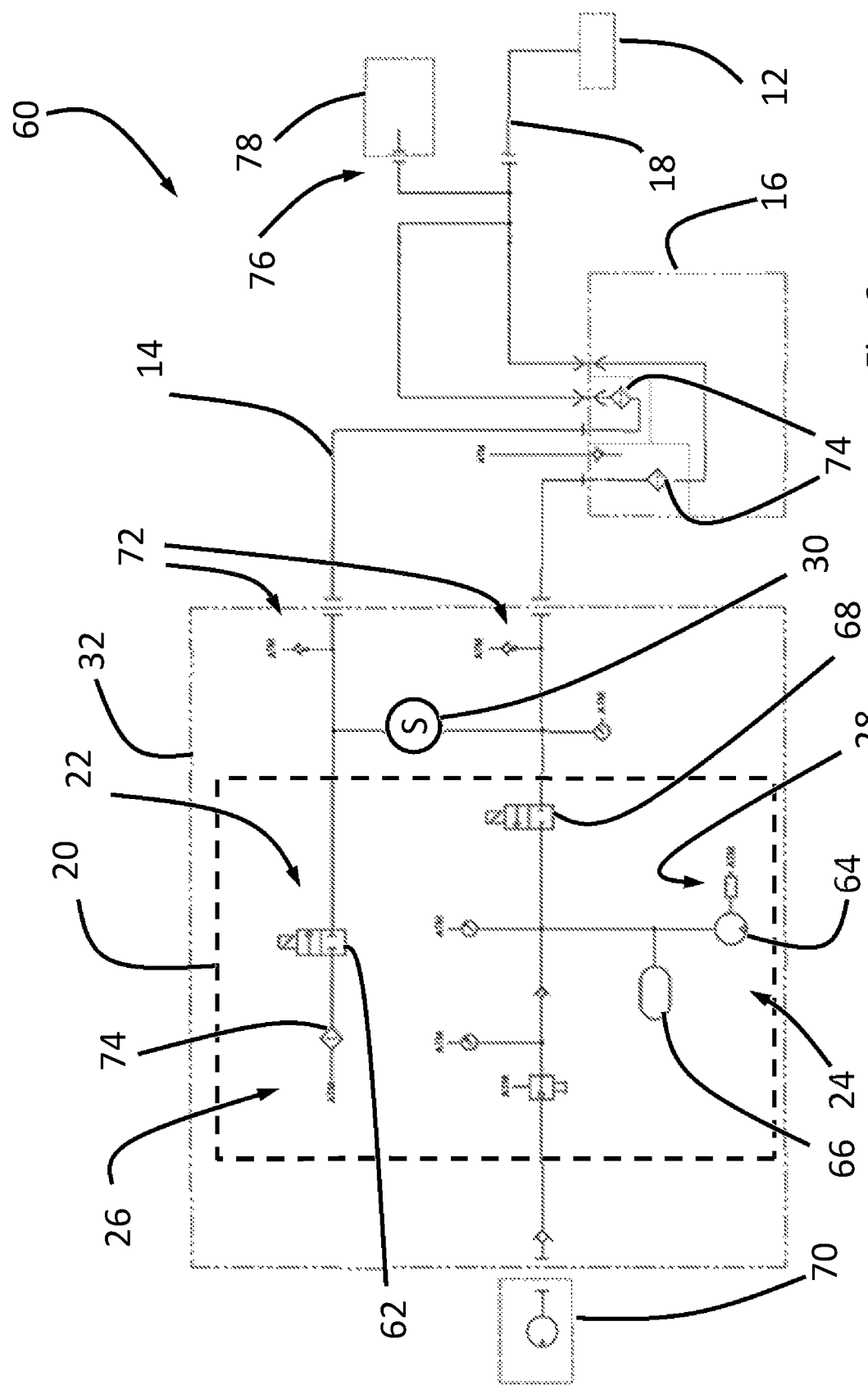
FIGS. 6-9 illustrate chest drain systems according to various embodiments disclosed herein.

FIGS. 6-9 illustrate various embodiments of chest drains. These embodiments are not intended to be in any way limiting, but instead, to provide example of modifications that may be made, or features or components that may be added or removed, any of which modifications, features, or combinations thereof, may be made, added, or removed from any other embodiments. Referring now to FIG. 6, a chest drain system 60 is illustrated, which shares several elements in common with the system 10, which shared or common elements are identified with the same reference numerals. For example, the system 60 is attached to a patient 12 via the chest tube 18 in order to collect fluids from the patient 12 in the canister 16, with the composition of fluid flow within the tubing circuit 14 sensed by the sensor 30. It is noted that these shared or common elements of any embodiment are not again described in full, since a description of each is already provided herein above, and thus the discussion of FIGS. 6-9 will concentrate on differences over the system 10.

While the system 60 also generally includes the circulation assembly 20, selective flow devices 22 and 24, the intake 26, and the exhaust 28 as part of the control unit 32, specific examples for components of the circulation assembly 20 and selective flow devices 22 and 24 are provided. More specifically, the system 60 includes an electronically controlled one-way valve 62 for the selective intake flow device 22. The selective exhaust flow device 24 in the system 60 includes a vacuum pump 64 and a vacuum accumulator 66. An electronically controlled one-way valve 68 may additionally be included to selectively permit and deny fluid communication between the pump 64 and/or the accumulator 66 with the rest of the system 10.

Advantageously, the accumulator 66 may be arranged having a preset capacity and used in conjunction with the valves 62 and 68 (e.g., which are simultaneously opened via instruction from the control unit 32) in order to pull a preset volume of fluid into the tubing circuit 14 via the intake 26 and through the tubing circuit 14 toward the accumulator, where excess fluid can be exhausted through the exhaust 28 (e.g., actively via the pump 64). As discussed above, the use of the accumulator 66 may be particularly advantageous in embodiments in which it is desired to know the displaced fluid volume, i.e., $V_{displaced}$, although it is to be understood that the accumulator 66 may be used in any other embodiment to facilitate operation of the circulation assembly 20. An external vacuum source 70, e.g., provided via a standard medical vacuum system in a hospital may alternatively and/or additionally be used with or for the exhaust flow device 24. It is reiterated that these specific examples of these components could take other forms, e.g., as described above with respect to the system 10, and that FIGS. 6-9 represent merely a few non-limiting embodiments.

The system 60 is illustrated as including various check valves 72 throughout the tubing circuit 14, e.g., to assist in maintaining a static or preset pressure within the system 60. One or more filters 74 may also be included at various locations along the tubing circuit 14. The filters 74 may be particularly advantageous for isolating the control unit 32 from contaminates and materials originating from the patient 12 in embodiments in which the control unit 32 is intended to be reusable. The filters 74 may also be used to prevent outside contaminates from the ambient environment from reaching the patient 12. A sampling port 76 may be included, e.g., to permit a syringe 78 or other device to sample fluid from the tubing circuit 14 and/or the chest tube 18.

Figure 7:
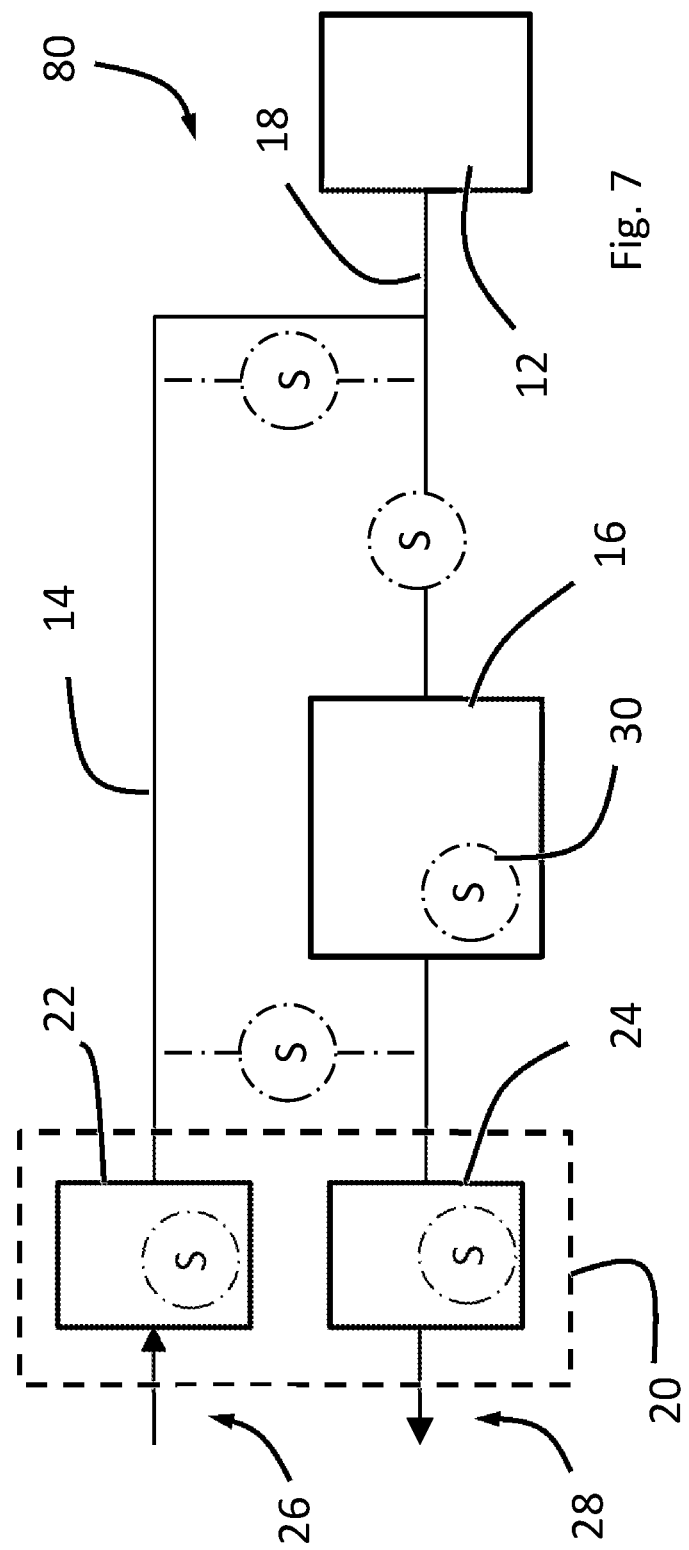

A system 80 according to another embodiment is illustrated in FIG. 7. Unlike the system 10, the system 80 does not include the control unit 32. Thus, this embodiment may be preferred if the entirety of the system 80 is intended to be disposable, unlike the system 10 in which the control unit 32 may be reusable. It is noted that elements of the control unit 32, such as a CPU, display, memory, etc. may be included in the selective flow devices 22 and/or 24 to facilitate operation of these components and thus operate in any manner discussed above, such as manually or upon receipt of an electronic signal instruction from a user, CPU, or a sensor upon sensing one or more parameters (e.g., pressure, pressure differential, reference fluid concentration, etc.).

Figure 8:
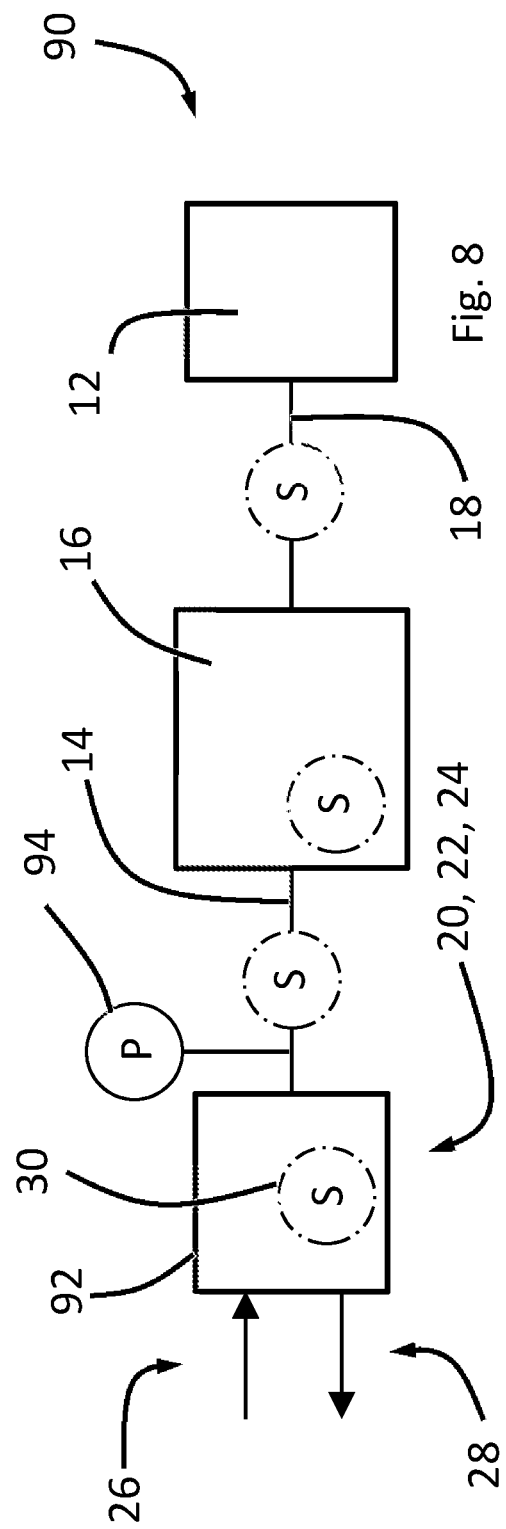
Figure 9:
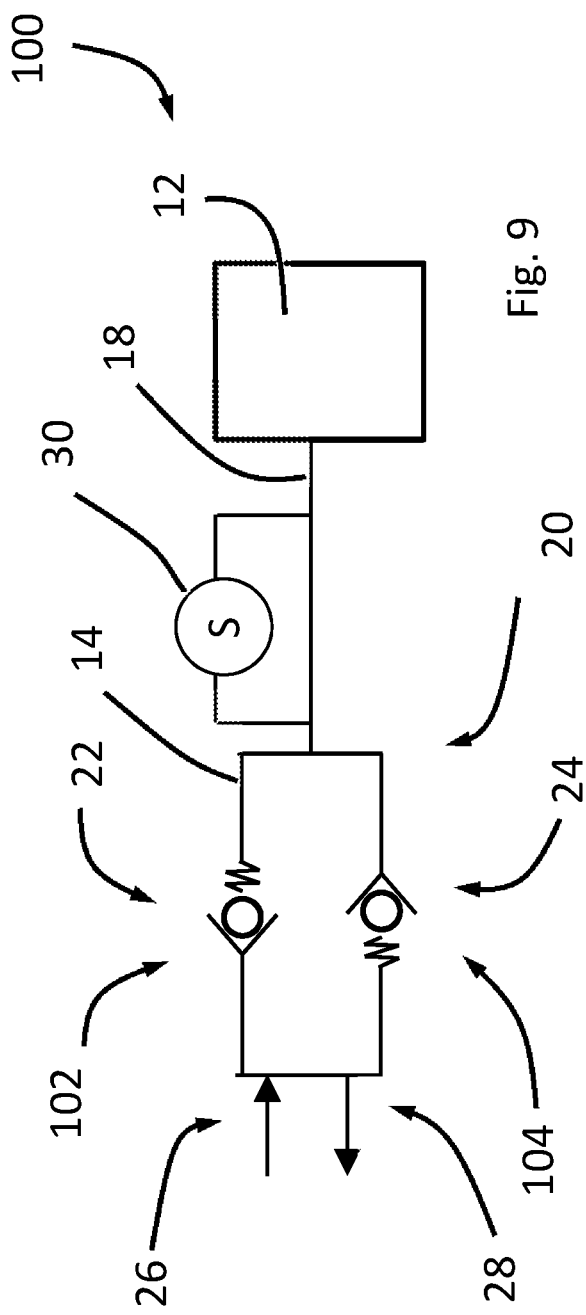

A system 90 is illustrated in FIG. 8 in order to show an example in which the circulation assembly 20 is combined in a single intake/exhaust device 92. That is, the device 92 combines the functions of both the devices 22 and 24 described above. The device 92 may be arranged as a three way valve that selectively connects the tubing circuit 14 to either the intake 26 or the exhaust 28. Alternatively, the device 92 may be arranged as a reversible pump, such that the intake 26 and the exhaust 28 are formed by the same port, opening, or aperture and the pump operates in opposite directions to either push fluid into the system 90 or to exhaust fluid out of the system 90. The previously described systems, i.e., the systems 10, 60, and 80, note that the circulation assembly 20 may be at least partially controlled by sensing one or more parameters other than reference gas concentration. To this end, the system 90 illustrates a pressure sensor 94 that can be used for this purpose, namely, to conduct a signal upon the sensor 94 measuring a corresponding pressure to control operation of the circulation assembly 20, namely, the device 92. For example, the device 92 could be arranged to fluidically connect the tubing circuit 14 to the intake 26 (or if the device 92 is arranged as a pump, operate the pump in a first direction) when or until a first pressure is achieved, and to fluidically connect the tubing circuit 14 to the exhaust (or if the device 92 is arranged as a pump, operate the pump in a second direction) when or until a second pressure is achieved A system 100 is illustrated in FIG. 9. The system 100 is included in order to show an example of a chest drain system that does not have a designated collection vessel, e.g., the canister 16, for collecting fluids from the patient 12. Instead, fluids from the patient 12 would simply pass through the chest tube 18 and/or the tubing circuit 14 and exit via the exhaust 28. The system 100 additionally includes a pair of check valves 102 and 104, which are arranged to open in opposite directions, and thus operate as the selective flow devices 22 and 24, respectively. Instead of being manually controlled, e.g., by action of a user, or electronically controlled, e.g., in response to a signal from a sensor measuring a corresponding parameter of the system, the valves 102 and 104 are intended to operate automatically in response to normal respiration of the patient 12. For example, the check valve 102 may be arranged to open in response to a first pressure that corresponds to the patient 12 inhaling, while the check valve 104 may be arranged to open in response to a second pressure that corresponds to an impermissibly high pressure within the system 100. In this way, the patient 12 may essentially act as a "pump" to pull fluid into the system 100 due to normal respiration. The sensor 30 may be connected to a control unit, display, etc., according to any of the embodiments disclosed or contemplated herein in order to perform the functions disclosed herein such as calculating values, manipulating data, displaying data or trend lines, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of using a chest drainage system comprising:
controlling fluid communication through an intake and an exhaust of a circulation assembly of the chest drainage system;
displacing a volume of fluid within the chest drainage system by selectively permitting fluid from an ambient environment into the chest drainage system via the intake and exhausting fluid from the chest drainage system via the exhaust; and
monitoring a concentration of a reference fluid in a fluid mixture within the chest drainage system with a sensor of the chest drainage system at a first time before the displacing and at a second time after the displacing.

2. The method of claim 1, wherein the chest drainage system comprises a central processing unit, the method further comprising communicating data measured by the sensor during the monitoring to the central processing unit.

3. The method of claim 2, further comprising comparing a first value of the concentration of the reference fluid measured at the first time to a second value of the concentration of the reference fluid measured at the second time.

4. The method of claim 2, wherein the displacing occurs during an operational cycle of the circulation assembly and the method comprises performing multiple operational cycles of the circulation assembly.

* * * * *